US005723675A

United States Patent [19]

Joo et al.

[11] Patent Number: 5,723,675
[45] Date of Patent: Mar. 3, 1998

[54] METHOD FOR PREPARING ANTHRAQUINONES

[75] Inventors: Young J. Joo; Jin-Eok Kim; Jeong-Im Won; Kum-Ui Hwang, all of Taejeon, Rep. of Korea

[73] Assignee: Korea Kumho Petrochemical Co., Ltd., Seoul, Rep. of Korea

[21] Appl. No.: 758,920

[22] Filed: Dec. 2, 1996

[30] Foreign Application Priority Data

May 16, 1996 [KR] Rep. of Korea ............ 96-16434

[51] Int. Cl.$^6$ ............................................. C07C 45/61
[52] U.S. Cl. .......................... 568/317; 568/312; 568/328
[58] Field of Search .................... 568/317, 312, 568/328, 320

[56] References Cited

PUBLICATIONS

Chem Rev 1993, 93, 741–761 Pindur "Acceleration & Selectivity Enhancement of Diels–Alder Reactions etc".
Liebigs Ann. Chem 1993, 905–909 Khanbabee, "Total Synthesis of Hallachrome & Related Anthraquinones".

*Primary Examiner*—C. Warren Ivy
*Assistant Examiner*—Jean F. Vollano
*Attorney, Agent, or Firm*—Harrison & Egbert

[57] ABSTRACT

A method for preparing anthraquinones, by which 1,4-benzoquinone or 1,4-naphthoquinone and 1,3-butadienes are subjected to a [2+4] Diels-Alder reaction and subsequently to oxidative dehydrogenation by using dimethylsulfoxide as a dehydrogenating agent in a single pot in the presence of a Lewis acid or Broensted acid shows high selectivity and yield.

5 Claims, No Drawings

METHOD FOR PREPARING ANTHRAQUINONES

BACKGROUND OF THE INVENTION

1. Field of the Invention

The present invention relates to a method for preparing anthraquinones which comprises being subjected to a [2+4] Diels-Alder reaction of 1,4-benzoquinone, or 1,4-naphthoquinone with 1,3-butadienes and simultaneously being subjected to oxidative dehydrogenation of them. More particularly, the present invention relates to a method for preparing anthraquinones which comprises being subjected to a [2+4] Diels-Alder reaction of 1,4-benzoquinone or 1,4-naphthoquinone as a dienophile with unsubstituted or substituted 1,3-butadienes to produce 1,4,4a,9a-tetrahydroanthraquinones. The product is then simultaneously dehydrogenated with the [2+4] Diels-Alder reaction, without pretreatment for a subsequent process such as separation or purification. The produced 1,4,4a,9a-tetrahydroanthraquinones are converted into anthraquinones by oxidative dehydrogenation, using dimethylsulfoxide (hereinafter referred to as "DMSO") as a dehydrogenating agent, and a Lewis acid or Broensted acid as a dehydrogenation catalyst as well.

2. Description of the Prior Art

Anthraquinones are well known to be used as a starting material for various anthraquinone dyes, and moreover as an important material for various dyes including acidic dyes, mordant dyes, vat dyes, and reactive dyes. Anthraquinones are also used to prepare hydrogen peroxide, taking advantage of their oxidation/reduction reactivity, as disclosed in Ullmann's Encyclopedia of Industrial Chemistry, vol. 2, pp 347–354 (1985), VCH, Germany. Hydrogen peroxide may be produced by reaction of peroxides with inorganic acids. Currently, however, hydrogen peroxide is mostly produced by autoxidation utilizing the oxidation/reduction reactivity of anthraquinones. Most of the patent literatures concerning anthraquinones relate to the preparation of hydrogen peroxide. Recently, there were disclosures in U.S. Pat. Nos. 5,374,339 (1995), 5,376,353 (1995), 5,399,333 (1995), and 5,435,985 (1995), Japanese Pat. Laid-Open Publication No. Heisei 6-191803 (1994), and EP No. 672,617 (1995).

Also, the principle for the preparation of hydrogen peroxide utilizing the oxidation/reduction reactivity of anthraquinone is used in the production of pulp for preparing paper. When pulp is produced, anthraquinone is added to remove or treat the lignin of pulp. This method has been researched, as disclosed in EP. Nos. 666,831 (1995) and 673,348 (1995) and PCT Nos. 94/10085 and 95/10480. Such research becomes a very important field.

As aromatic compounds of fine chemicals, anthraquinones are very important and are mainly prepared by the following three methods:

1. by oxidizing anthracene;
2. by synthesis from phthalic anhydride and benzene, using Friedel-Crafts reaction; and
3. by being subjected to the [2+4] Diels-Alder reaction of 1,4-naphthoquinone with 1,3-butadienes, followed by dehydrogenation.

The oldest method is item 1), by oxidizing anthracene. This can be done by oxidizing anthracene using chrome as an oxidant in the liquid phase, or oxidizing anthracene using oxygen as an oxidant in the gas phase. In the case of the liquid phase reaction, it is difficult to dispose of the waste containing chrome. In the case of the gas phase reaction using oxygen, the reactivity is low and thus the reaction is performed in high temperatures. For these reasons, by-products are more produced in the gas phase reaction and facilities for purifying waste air are very complicated. For the Friedel-Crafts reaction of phthalic anhydride, item 2), aluminum trichloride ($AlCl_3$) is used as a catalyst and its disposal is also seriously problematic. Thus, presently, there has been an intensive research on the method of item 3) which comprises being subjected to the [2+4] Diels-Alder reaction of 1,4-naphthoquinone and 1,3-butadiene and then dehydrogenating the resulting 1,4,4a,9a-tetrahydroanthraquinone.

As a typical [2+4] Diels-Alder reaction, the [2+4] Diels-Alder reaction of 1,4-naphthoquinone with 1,3-butadiene capable of producing 1,4,4a,9a-tetrahydroanthraquinone is well known. There have been many patents concerning such a reaction, including Japanese Pat. Laid-Open Publication Nos. Sho. 51-8256, 51-8257, 51-54540, 51-118754 and 51-138666, published in 1976. The reason why a method utilizing a [2+4] Diels-Alder reaction is widely applied is that the reaction is a kind of thermally allowed reaction. That is, the [2+4] Diels-Alder reaction can be performed simply by elevating the reaction temperature, without using any catalyst. Therefore, the generation of pollution is decreased. In addition, the [2+4] Diels-Alder reaction is superior in selectivity, so that no by-products are generated.

As explained above, the [2+4] Diels-Alder reaction of 1,4-naphthoquinone and 1,3-butadiene does not need particular catalysts and produces less by-products other than 1,4,4a,9a-tetrahydroanthraquinone. However, the pretreatment for separating 1,4,4a,9a-tetrahydroanthraquinone from these by-products to dehydrogenate 1,4,4a,9a-tetrahydroanthraquinone or for dehydrogenating in a single pot is troublesome. For example, U.S. Pat. No. 5,387,704 (1995) and Japanese Pat. Publication No. Hei. 6-047564 (1994) disclose that for dehydrogenation using a catalyst and oxygen, unreacted 1,3-butadiene has to be removed or 1,4,4a,9a-tetrahydroanthraquinone has to be separated, so as to exclude the possibility of explosion.

SUMMARY OF THE INVENTION

The above problems may be solved by a method for preparing anthraquinones which comprises being subjected to a [2+4] Diels-Alder reaction of 1,4-benzoquinone or 1,4-naphthoquinone and 1,3-butadienes, simultaneously while being subjected to an oxidative dehydrogenation using dimethylsulfoxide as a dehydrogenating agent and a Lewis acid or Broensted acid as a dehydrogenation catalyst.

1,4,4a,9a-tetrahydroanthraquinones, the products of the [2+4] Diels-Alder reaction of 1,4-benzoquinone or 1,4-naphthoquinone with 1,3-butadienes, are stable compounds which can be separated, but are more unstable than other anthraquinones in thermodynamics. Thus, the present invention takes such thermodynamical stability into account, so that 1,4,4a,9a-tetrahydroanthraquinone may be subjected as such to oxidative dehydrogenation in a single pot without its separation to prepare anthraquinones. Thus the process is shortened.

Accordingly, it is an object to provide a method for preparing anthraquinones which comprises dehydrogenating 1,4,4a,9a-tetrahydroanthraquinones obtained through a [2+4] Diels-Alder reaction of 1,4-naphthoquinone or 1,4-benzoquinone with 1,3-butadienes, wherein the [2+4] Diels-Alder reaction and oxidative dehydrogenation are, in sequence, carried out in a single pot by using DMSO, not only as a dehydrogenating agent but also as a solvent for said

[2+4] Diels-Alder reaction and using a Lewis catalyst or Broensted acid as an oxidative catalyst for dehydrogenation.

DETAILED DESCRIPTION OF THE INVENTION

The present invention relates to a method for preparing anthraquiinones, in which 1,4,4a,9a-tetrahydroanthraquinones are formed through a [2+4] Diels-Alder reaction of 1,4-naphthoquinone or 1,4-benzoquinone and 1,3-butadiene, and subjected to dehydrogenation in a single pot without further pretreatment, such as isolation or purification.

In accordance with the present invention, in order to perform the [2+4] Diels-Alder reaction and the dehydrogenation in a single pot, a mild oxidant is essential, which is not involved in the Diels-Alder reaction but participates only in the dehydrogenation. The present inventors found that DMSO satisfied this requirement.

It is stated in Synthesis (1990) pp. 857–870 that since the oxidation activity of DMSO is very low, it can usually be maintained only by using a strong base or being activated. In particular, DMSO dissolves quinones with low solubility, and has a good solubility to the acid catalyst which plays the role of catalyst in the [2+4] Diels-Alder reaction as well. In this way, the Diels-Alder reaction is promoted and also anthraquinones, the products by oxidative dehydrogenation, can be obtained in high yield. Therefore, DMSO is used as both a reaction solvent and an oxidant for the preparation of anthraquinones, in accordance with the present invention.

The 1,3-butadienes used in the present invention include 1,3-butadiene, isoprene and 2,3-dimethyl-1,3-butadiene. According to the present invention, when 1,4-benzoquinone is reacted with 1,3-butadiene, isoprene or 2,3-dimethyl-1,3-butadiene, the resulting anthraquinones include anthraquinone, 2,7-dimethyl-anthraquinone and 2,3,6,7-tetramethyl-anthraquinone while, when 1,4-naphthoquinone is reacted with 1,3-butadiene, isoprene, and/or 2,3-dimethyl-anthraquinone, the resulting anthraquinones include anthraquinone, 2-methylanthraquinone and 2,3-dimethyl-anthraquinone.

The oxidative dehydrogenation using a Lewis acid, such as $SnCl_4$, $ZnCl_2$ and $FeCl_3$, or a Broensted acid, such as p-toluenesulfonic acid, as an acid catalyst may be utilized to prepare anthraquinones. Although all the catalysts used in the Lewis acids and Broensted acids are possible, $SnCl_4$ allows the anthraquinones to be prepared at the best conversion rate and selectivity among these catalysts (Example III).

The amount of catalyst used is up to 50.0% by weight relative to 1,4-benzoquinone or 1,4-naphthoquinone. The amount is not particularly limited, but the reaction occures, provided that a small amount of catalyst to represent catalyst activity is added. Thus, it is suitable in the range of 0.01 to 50.0% by weight.

The reaction temperature is in the range of 80° to 160° C., and more preferably between 110° and 160° C. As the reaction temperature increases, the reaction is proceeded in higher yield within a shorter time.

Such oxidative dehydrogenation, utilizing DMSO, is not known, but where intermediates are thermodynamically less stable than the starting materials, as in the present invention, it was found that DMSO was also usable as a good oxidant or oxidative dehydrogenating agent. In particular, in the case of having a carbonyl group such as 1,4,4a,9a-tetrahydroanthraquinones and 1,4-dihydroanthraquinones intermediates, it is helpful to the production of anthraquinones which become thermodynamically stable, for the carbonyl group to form a complex by a Lewis acid or a Broensted acid. From this fact, the acid catalyst is expected to be a good reaction promoter.

The present invention takes advantage of a typical homogeneous catalyst system and uses a reactor which can be pressurized in batch.

In particular, in an aspect according to the present invention, 1,4-benzoquinone or 1,4-naphthoqhinone was dissolved in DMSO in a flask reactor and then reacted with 1,3-butadienes using an acid catalyst while injecting the 1,3-butadienes through a syringe. In this case, the reaction proceeded so that the selectivity of 1,3-butadienes into anthraquinones was at a level of about 50%. In contrast, when a pressure reactor was used, the reaction proceeded in a selectivity rate of 99% or more. In addition, the reaction using oxygen instead of an acid catalyst resulted in that the main product was not naphthoquinones and anthraquinones, but 5,8-dihydro-1,4-naphthalene diol. Thus, all the experiments of the present invention were carried out in a pressure reactor.

The analytical data of the reactants are identified by NMR spectra and GC-MSD. Quantitative analytical data are identified using gas chromatography under the following conditions and, for component ratios, values are calculated in terms of area ratios:

Capillary column: ULTRA 1(Crosslinked Methyl Silicone Gum) 50 m×0.22 mm×0.33 μm

Carrier: nitrogen

Head pressure: 18 psig

Oven: 150° C. (2 min) to 280° C., beta=20° C./min

Injection Temp.: 280° C.

Detector & Temp.: FID (280° C.)

Split ratio: 50:1

Makeup gas flowrate: 38 ml

The present invention is embodied in the following examples which are not to be construed to limit the present invention.

EXAMPLE I

In a 250 ml reactor being equipped with a cooler and stirrer, which could be pressurized, 2.0 g (18.5 mmol) of 1,4-benzoquinone, 4.1 ml (3.0 g. 37.0 mmol) of 2,3-dimethyl-1,3-butadiene, and 1.0 g. (2.8 mmol) of stannic chloride ($SnCl_4$) were dissolved in 80 ml of DMSO, while stirring. The mixture was reacted for 1 hr while elevating the temperature of the reactor up to 140° C. The initial reaction pressure at 140° C. was 35 psig. A certain amount of the reactants was taken, dissolved in chloroform, washed twice with water and dried over anhydrous sodium sulfate. The dried chloroform solution was distilled under reduced pressure and the residue was identified and analyzed by using NMR spectra and gas chromatography. The results are given as shown in Table 1 below. In Table 1, the term "conversion" means the percentage of the amount converted into an aromatic compound based on the amount of 1,4-benzoquinone left. The term "selectivity" means the content of 2,3,6,7-tetramethylanthraquinone relative to the aromatic compound in the products. The conversion and the selectivity according to the reaction temperature are also given in Table 1. From Table 1, it can be found that the [2+4] Diels-Alder reaction can be performed at 80° C., but the oxidative dehydrogenation is slowly performed even at 110° C. In particular, the selectivity was so low that in the following Examples from 2 to 6 the reaction was carried out at the reaction temperature of 140° C. for 1 hr of reaction time. Herein, stannic chloride was used as a catalyst.

TABLE 1

| Conversion and Selectivity according to Reaction Temp. ||
| --- | --- |
| Rxn. Temp. | Conversion/Selectivity |
| 80° C. | 100%/11% |
| 110° C. | 100%/32% |
| 140° C. | 100%/81% |
| 160° C. | 100%/96% |

EXAMPLE II

The reaction was performed in the manner similar to Example I, except for changing the amount of the catalyst. The results are given as shown in Table 2 below. As apparent from Table 2, the catalyst enhances the conversion and selectivity of the reaction.

TABLE 2

| Conversion and Selectivity according to Change in Catalyst Amount ||
| --- | --- |
| Catalyst Amount | Conversion/Selectivity |
| 0 g | 69%/18% |
| 0.2 g | 73%/56% |
| 0.5 g | 87%/63% |
| 1 g | 100%/81% |

EXAMPLE III

The reaction was performed in the manner similar to Example I, except for changing the kind of catalyst. The results are given as shown in Table 3 below. As apparent from Table 3, both Lewis acid and Broensted acid can be used as a catalyst.

TABLE 3

| Conversion and Selectivity according to Kind of Catalyst ||
| --- | --- |
| Kind of Catalyst | Conversion/Selectivity |
| $SnCl_4$ | 100%/81% |
| $ZnCl_2$ | 95%/35% |
| $FeCl_3$ | 14%/72% |
| p-Toluenesulfonic acid | 33%/100% |

EXAMPLE IV

The reaction was performed in the manner similar to Example I, except for changing molar ratios of 1,4-benzoquinone to 2,3-dimethyl-1,3-butadiene. The results are given as shown in Table 4 below. The conversion and the selectivity were based on minimal amounts.

TABLE 4

| Conversion and Selectivity according to Change in Molar Ratio of 1,4-benzoquinone/2,3-dimethyl-1,3-butadiene ||
| --- | --- |
| Molar Ratio | Conversion/Selectivity |
| 1.0 | 64%/34% |
| 0.5 | 100%/81% |
| 0.25 | 100%/88% |

EXAMPLE V

The reaction was performed in the manner similar to Example I, except for using 1,3-butadiene or isoprene instead of 2,3-dimethyl-1,3-butadiene. The results are given as shown in Table 5 below.

TABLE 5

| Conversion and Selectivity according to Kind of 1,3-Butadiene ||
| --- | --- |
| Kind | Conversion/Selectivity |
| 1,3-butadiene | 100%/81% |
| isoprene | 100%/64% |
| 2,3-dimethyl-1,3-butadiene | 100%/81% |

EXAMPLE VI

The reaction was performed in the manner similar to Example I, except that 4.2 g (26.5 mmol) of naphthoquinone was used instead of benzoquinone, and 3.0 ml (2.2 g, 26.5 mmol) of 2,3-dimethyl-1,3-butadiene and 1.9 g of stannic chloride was dissolved in 80 ml of DMSO while stirring. Then the temperature of the reactor was raised up to 130° C. The results are given as shown in Table 6 below.

TABLE 6

| Rxn. Temp. | Conversion/Selectivity |
| --- | --- |
| 80° C. | 100%/23% |
| 110° C. | 100%/58% |
| 130° C. | 100%/99% |

EXAMPLE VII

The reaction was performed in the manner similar to Example VI, except for changing the amount of the catalyst. The results are given as shown in Table 7 below. As apparent from Table 7, the catalyst enhances the selectivity of the reaction.

TABLE 7

| Conversion and Selectivity according to Change in Catalyst Amount ||
| --- | --- |
| Catalyst Amount | Conversion/Selectivity |
| 0 g | 100%/75% |
| 1 g | 100%/98% |
| 1.9 g | 100%/99% |
| 3 g | 100%/99% |

EXAMPLE VIII

The reaction was performed in the manner similar to Example VI, except for changing the kind of catalyst. The results are given as shown in Table 8 below. As apparent from Table 8, both Lewis acid and Broensted acid can be used as a catalyst.

TABLE 8

| Conversion and Selectivity according to Kind of Catalyst ||
| --- | --- |
| Kind of Catalyst | Conversion/Selectivity |
| $SnCl_4$ | 100%/98% |
| $ZnCl_2$ | 96%/96% |
| $FeCl_3$ | 95%/92% |
| p-Toluenesulfonic acid | 95%/90% |

EXAMPLE IX

The reaction was performed in the manner similar to Example VI, except for using 1,3-butadiene or isoprene instead of 2,3-dimethyl-1,3-butadiene. The results are given as shown in Table 9 below.

TABLE 9

Conversion and Selectivity according to Kind of 1,3-Butadiene

| Kind | Conversion/Selectivity |
|---|---|
| 1,3-butadiene | 100%/93% |
| isoprene | 100%/95% |
| 2,3-dimethyl-1,3-butadiene | 100%/99% |

The present invention has been described in an illustrative manner, and it is to be understood that the terminology used is intended to be in the nature of description rather than of limitation.

Many modifications and variations of the present invention are possible in light of the above teachings. Therefore, it is to be understood that within the scope of the appended claims, the invention may be practiced otherwise than as specifically described.

What is claimed is:

1. A method for preparing anthraquinones unsubstituted or substituted with at least one $C_1$–$C_4$ alkyl group through a [2+4] Diels-Alder reaction of 1,4-naphthoquinone or 1,4-benzoquinone with 1,3-butadienes unsubstituted or substituted with at least one C—C alkyl group and a dehydrogenation of 1,4,4a,9a-tetrahydroanthraquinones obtained from the [2+4] Diels-Alder reaction using a Lewis acid or Broensted acid as an oxidative catalyst for dehydrogenation, the method comprising the step of:

carrying out simultaneously the [2+4] Diels-Alder reaction and the oxidative dehydrogenation in a single pot by using dimethylsulfoxide as a dehydrogenating agent and as a solvent for the [2+4] Diels-Alder reaction.

2. The method in accordance with claim 1, wherein said 1,3-butadienes are selected from the group consisting of 1,3-butadienes, isoprene, and 2,3-dimethyl-1,3-butadiene, and said anthraquinones are selected from the group consisting of anthraquinone, 2,7-dimethylanthraquinone, 2,3,6,7-tetramethylanthraquinone, 2-methylanthraquinone and 2,3-dimethylanthraquinone.

3. The method in accordance with claim 1, wherein the Lewis acid is selected from the group consisting of $SnCl_4$, $ZnCl_2$ and $FeCl_3$ and the Broensted acid is p-toluenesulfonic acid.

4. The method in accordance with claim 1, wherein the reaction temperature for the [2+4] Diels-Alder reaction and the oxidative dehydrogenation is between 110° C. and 160° C., inclusive.

5. The method in accordance with claim 1, wherein the oxidative catalyst is used in an amount of 0.01 to 50.0% by weight relative to the weight of 1,4-benzoquinone or 1,4-naphthoquinone.

* * * * *